(12) United States Patent
Jasti et al.

(10) Patent No.: US 7,297,711 B2
(45) Date of Patent: Nov. 20, 2007

(54) ARYLALKYL INDOLES HAVING SEROTONIN RECEPTOR AFFINITY USEFUL AS THERAPEUTIC AGENTS, PROCESS FOR THEIR PREPARATION AND PHARMACEUTICAL COMPOSITIONS CONTAINING THEM

(75) Inventors: Venkateswarlu Jasti, Hyderabad (IN); Venkata Satya Nirogi Ramakrishna, Hyderabad (IN); Rama Sastri Kambhampati, Hyderabad (IN); Srinivasa Reddy Battula, Hyderabad (IN); Venkata Satya Veerabhadra Vadlamudi Rao, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 0 days.

(21) Appl. No.: 10/518,624

(22) PCT Filed: Jun. 19, 2003

(86) PCT No.: PCT/IN03/00224

§ 371 (c)(1),
(2), (4) Date: May 13, 2005

(87) PCT Pub. No.: WO04/000845

PCT Pub. Date: Dec. 31, 2003

(65) Prior Publication Data
US 2005/0203103 A1    Sep. 15, 2005

(30) Foreign Application Priority Data
Jun. 21, 2002 (IN) .................................. 476/2002

(51) Int. Cl.
*A61K 31/403* (2006.01)
*A61K 31/454* (2006.01)
*A61K 31/496* (2006.01)
*C07D 209/58* (2006.01)
*C07D 401/14* (2006.01)
*C07D 403/06* (2006.01)

(52) U.S. Cl. ................. 514/410; 514/254.08; 514/323; 548/420; 546/200; 544/372

(58) Field of Classification Search ................ 548/420; 546/200; 544/238, 372; 514/254.08, 323, 514/410
See application file for complete search history.

(56) References Cited

U.S. PATENT DOCUMENTS

| 4,839,377 A | 6/1989 | Bays et al. |
| 4,855,314 A | 8/1989 | Oxford et al. |

FOREIGN PATENT DOCUMENTS

| EP | 303506 | 2/1989 |
| EP | 313397 | 4/1989 |
| EP | 354777 | 2/1991 |
| EP | 438230 | 7/1991 |
| EP | 457701 | 11/1991 |
| EP | 497512 | 8/1992 |
| GB | 2035310 | 6/1980 |
| WO | 91/18897 | 12/1991 |
| WO | 93/00086 | 1/1993 |
| WO | 93/23396 | 11/1993 |
| WO | 94/06769 | 3/1994 |

OTHER PUBLICATIONS

Morissette et al. Advanced Drug Delivery Reviews 2004, 56, 275-300.*
Kozikowski et al. Tetrahedron Lett. 1991, 32(28), 3317-20.*
Barnes et al. Neuropharmacology 1999, 38, 1083-1152.*
Bassiony et al. Psychosomatics 2003, 44(5), 388-401.*
Gershon, M. D. Ailment Pharmacol. Ther. 2004, 20(suppl. 7), 3-14.*
Fuller, R.W., Drugs Acting on Serotonergic Neuronal Systems, Biology of Serotonergic Transmission, John Wiley & Sons Ltd. (1982), 221-247.
Gershon M.D. et al., The periphal actions of 5-Hydroxytryptamine (1989), 246.
Saxena P.R. et al., Journal of Cardiovascular Pharmacology (1990), supplement 7,15.
Glennon et al., Neuroscience and Behavioral Reviews (1990), 14, 35.
Hoyer D. et al., Pharmacol. Rev. (1994), 46, 157-203.
Ruat M. et al., Biochem. Biophys. Res. Com. (1993), 193, 269-276.
Roth et al., J. Pharm. Exp. Therapeut. (1994), 268, 1403-1410.
Sleight et al., Exp. Opin Ther. Patents (1998), 8, 1217-1224.
Bourson et al, Brit J. Pharmacol. (1998), 125, 1562-1566.
Boess et al, Mol. Pharmacol., 1998, 54, 577-583.
Sleight et al., Brit J. Pharmacol. (1998), 124, 556-562.
Yoshioka et al, Life Sciences (1998), 17/18, 1473-1477.
Schoeffter P. et al. "SDZ216-525, a selective and potent 5-HT1A receptor antagonist" European Journal of Pharmacology, 224, 251-257 (1993).

* cited by examiner

*Primary Examiner*—Kamal A. Saeed
*Assistant Examiner*—Jason M. Nolan
(74) *Attorney, Agent, or Firm*—Darby & Darby

(57) ABSTRACT

The present invention relates to novel tetracyclic arylalkyl indoles, their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them. This invention particularly relates to novel tetracyclic arylalkyl of the general formula (I), their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them. This invention also relates to process/es for preparing such compound/s of general formula (I), composition/s containing effective amount/s of such a compound and the use of such a compound/composition in therapy.

12 Claims, No Drawings

ARYLALKYL INDOLES HAVING SEROTONIN RECEPTOR AFFINITY USEFUL AS THERAPEUTIC AGENTS, PROCESS FOR THEIR PREPARATION AND PHARMACEUTICAL COMPOSITIONS CONTAINING THEM

FIELD OF INVENTION

This application is a National Stage Application under 35 U.S.C. §371 of PCT International Application No. PCT/IN03/00224, filed Jun. 19, 2003, and claims priority of Indian Patent Application No. 476/MAS/2002, filed Jun. 21, 2002.

The present invention relates to novel tetracyclic arylalkyl indoles, their derivatives their analogues, their tautomeric forms, their stereoisomers, their polymorphs, their pharmaceutically acceptable salts, their pharmaceutically acceptable solvates, novel intermediates described herein and pharmaceutically acceptable compositions containing them.

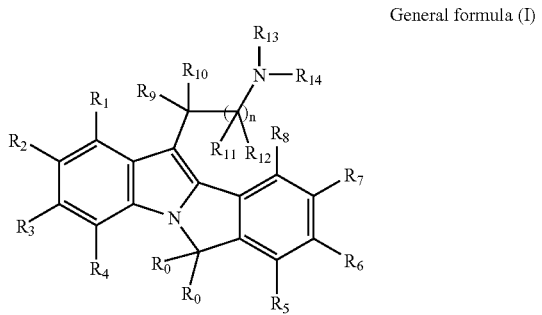

General formula (I)

The present invention also relates to the process for preparing the compounds of general formula (I), their derivatives, their analogs, their tautomeric forms, their stereoisomers, their geometric forms, their N-oxides, their polymorphs, their pharmaceutically acceptable salts, their pharmaceutically acceptable solvates, novel intermediates described herein and pharmaceutically acceptable compositions containing them.

The compounds of the general formula (I) of this invention are 5-HT (Serotonin) ligands e.g. agonists or antagonists.

Thus, compounds of general formula (I) of this invention are useful for treating diseases wherein activity of either 5-HT (Serotonin) and/or melatonin is modulated to obtain the desired effect. Specifically, the compounds of this invention are useful in the treatment and/or prophylaxis of psychosis, paraphrenia, psychotic depression, mania, schizophrenia, schizophreniform disorders, anxiety, migraine headache, depression, drug addiction, convulsive disorders, personality disorders, hypertension, autism, post-traumatic stress syndrome, alcoholism, panic attacks, obsessive-compulsive disorders.

The compounds of general formula (I) of this invention are also useful to treat psychotic, affective, vegetative and psychomotor symptoms of schizophrenia and the extrapyramidal motor side effects of other antipsychotic drugs.

The compounds of general formula (I) of this invention are also useful to treat neurodegenerative disorders like Alzheimer's disease, Parkinsonism and Huntington's chorea and chemotherapy-induced vomiting. The compounds of general formula (I) of this invention are also useful in modulation of eating behavior and thus are useful in reducing the morbidity and mortality associated with excess weight.

BACKGROUND OF THE INVENTION

Many diseases of the central nervous system are influenced by the adrenergic, the dopaminergic and the serotenergic neurotransmitter systems. Serotonin has been implicated in a number of diseases and conditions, which originate in the central nervous system. These include diseases and conditions related to sleeping, eating, perceiving pain, controlling body temperature, controlling blood pressure, depression, anxiety, schizophrenia and other bodily states. (References: Fuller, R. W., Drugs Acting on Serotonergic Neuronal Systems, Biology of Serotonergic Transmission, John Wiley & Sons Ltd. (1982), 221-247; Boullin D. J., Serotonin in Mental abnormalities (1978), 1, 316; Barchas J. et. al., Serotonin and Behavior (1973)). Serotonin also plays an important role in the peripheral systems, such as the gastrointestinal system, where it has been found to mediate a variety of contractile, secretory and electrophysiologic effects.

Due to the broad distribution of serotonin within the body, there is lot of interest and use, in the drugs that affect serotoriergic systems. Particularly, preferred are the compounds which have receptor specific agonism and/or antagonism for the treatment of a wide range of disorders, including anxiety, depression, hypertension, migraine, obesity, compulsive disorders, schizophrenia, autism, neurodegenerative disorders like Alzheimer's disease, Parkinsonism and Huntington's chorea and chemotherapy-induced vomiting (References: Gershon M. D. et. al., The peripheral actions of 5-Hydroxytryptamine (1989), 246; Saxena P. R. et. al., Journal of Cardiovascular Pharmacology (1990), supplement 7, 15).

The major classes of serotonin receptors ($5\text{-HT}_{1\text{-}7}$) contain fourteen to eighteen separate receptors that have been formally classified (References: Glennon et al, Neuroscience and Behavioral Reviews (1990), 14, 35 and Hoyer D. et al, Pharmacol. Rev. (1994), 46, 157-203). Recently discovered information regarding sub-type identity, distribution, structure and function suggests that it is possible to identify novel, sub-type specific agents having improved therapeutic profiles with lesser side effects. The $5\text{-HT}_6$ receptor was identified in 1993 (References: Monsma et al, Mol. Pharmacol. (1993), 43, 320-327 and Ruat M. et al, Biochem. Biophys. Res. Com. (1993), 193, 269-276). Several antidepressants and atypical antipsychotics bind to the $5\text{-HT}_6$ receptor with high affinity and this binding may be a factor in their profile of activities (References: Roth et al, J. Pharm. Exp. Therapeut. (1994), 268, 1403-1410; Sleight et al, Exp. Opin. Ther. Patents (1998), 8, 1217-1224; Bourson et al, Brit. J. Pharmacol. (1998), 125, 1562-1566; Boess et al, Mol. Pharmacol., 1998, 54, 577-583; Sleight et al, Brit. J. Pharmacol. (1998), 124, 556-562). In addition, $5\text{-HT}_6$ receptor has been linked to generalized stress and anxiety states (Reference: Yoshioka et al, Life Sciences (1998), 17/18, 1473-1477). Together these studies and observations suggest that compounds that antagonize the $5\text{-HT}_6$ receptor will be useful in treating various disorders of the central nervous system.

U.S. Pat. Nos. 4,839,377 and 4,855,314 refer to 5-substituted 3-aminoalkyl indoles. The compounds are said to be useful for the treatment of migraine.

British Patent 2,035,310 refers to 3-aminoalkyl-1 H-indole-5-thioamides and carboxamides. The compounds are said to be useful in treating hypertension, Raymond's disease and migraine.

European Patent Publication 303,506 refers to 3-polyhydropyridyl-5-substituted-1H-indoles. The compounds are said to have 5-$HT_1$ receptor agonists and vasoconstrictor activity and to be useful in treating migraine. European Patent Publication 354,777 refers to N-piperidinylindolyl-ethyl-alkane sulfonamide derivatives. The compounds are said to be 5-$HT_1$ receptor agonists and have vasoconstrictor activity and are useful in treating cephalic pain.

European Patent Publication 438,230, refers to indole-substituted five-membered heteroaromatic compounds. The compounds are said to have "5-$HT_1$-like" receptor agonist activity and to be useful in the treatment of migraine and other disorders for which a selective agonist of these receptors is indicated.

European Patent Publication 313,397 refers to 5-heterocyclic indole derivatives. The compounds are said to have exceptional properties for the treatment and prophylaxis of migraine, cluster headache and headache associated with vascular disorders. These compounds are also said to have exceptional "5-$HT_1$-like" receptor agonism.

International Patent Publication WO 91/18897, refers to 5-heterocyclic indole derivatives. The compounds are said to have exceptional properties for the treatment and prophylaxis of migraine, cluster headache, and headache associated with vascular disorders. These compounds are also said to have exceptional "5-$HT_1$-like" receptor agonism.

European Patent Publication 457,701 refers to aryloxy amine derivatives as having high affinity for 5-$HT_{1D}$ serotonin receptors. These compounds are said to be useful for treating diseases related to serotonin receptor dysfunction, for example, migraine.

European Patent Publication 497,512 A2, refers to a class of imidazole, triazole and tetrazole derivatives which are selective agonists for "5-$HT_1$-like" receptors. These compounds are said to be useful for treating migraine and associated disorders.

International Patent Publication WO 93/00086, describes a series of tetrahydrocarbazole derivatives, as 5-$HT_1$ receptor agonists, useful for the treatment of migraine and related conditions.

International Patent Publication WO 93/23396, refers to fused imidazole and triazole derivatives as 5-$HT_1$ receptor agonists, for the treatment of migraine and other disorders.

Schoeffler P. et al. refer to methyl 4-{4-[4-(1,1,3-trioxo-2H-1,2-benzoisothiazol-2-yl)butyl]-1-piperazinyl}1H-indole-3-carboxylate as a selective antagonist for the 5-$HT_{1A}$ receptor in their paper "SDZ216-525, a selective and potent 5-$HT_{1A}$ receptor antagonist" European Journal of Pharmacology, 244, 251-257 (1993).

International Patent Publication WO 94/06769, refers to 2-substituted-4-piperazine-benzothiophene derivatives that are serotonin 5-$HT_{1A}$ and 5-$HT_{1D}$ receptor agents useful in the treatment of anxiety, depression, migraine, stroke, angina and hypertension.

SUMMARY OF THE INVENTION

The present invention relates to novel tetracyclic arylalkyl, their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them.

More particularly, the present invention relates to novel tetracyclic arylalkyl of the general formula (I), their derivatives, their analogs, their tautomeric forms, their stereoisomers, their polymorphs, their pharmaceutically acceptable salts, their pharmaceutically acceptable solvates, novel intermediates described herein and pharmaceutically acceptable compositions containing them and use of these compounds in medicine.

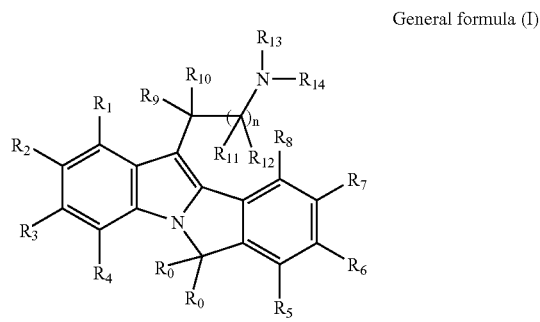

General formula (I)

wherein $R_0$ is either hydrogen or linear or branched ($C_1$-$C_2$) alkyl;

$R_1$, $R_2$, $R_3$, $R_4$, $R_5$, $R_6$, $R_7$, $R_8$, $R_9$, $R_{10}$, $R_{11}$ and $R_{12}$ may be same or different and each independently represent hydrogen, halogen, perhaloalkyl, amino, substituted or unsubstituted groups such as linear or branched ($C_1$-$C_{12}$)alkyl, ($C_3$-$C_7$)cycloalkyl, ($C_1$-$C_{12}$)alkoxy, cyclo($C_3$-$C_7$)alkoxy, aryl, aryloxy, aralkyl, aralkoxy, heterocyclyl, heteroaralkyl, acyl, acyloxy, acylamino, monoalkylamino, dialkylamino, arylamino, diarylamino, aralkylamino, hydroxyalkyl, aminoalkyl, monoalkylaminoalkyl, dialkylaminoalkyl, alkoxyalkyl, alkylthio, dialkylaminocarbonylamino, carboxylic acid and its derivatives, $R_{13}$ and $R_{14}$ may be same or different and each independently represents hydrogen, substituted or unsubstituted groups such as linear or branched ($C_1$-$C_{12}$)alkyl, ($C_2$-$C_{12}$) alkenyl, ($C_3$-$C_7$)cycloalkyl, ($C_3$-$C_7$)cycloalkenyl, bicycloalkyl, bicycloalkenyl, aryl, aralkyl, optionally $R_{13}$ and $R_{14}$ along with the nitrogen atom, may form a 3, 4, 5, 6 or 7-membered heterocyclic ring, wherein the ring may be further substituted, and it may have either one, two or three double bonds or "additional heteroatoms", as defined above.

"n" is an integer ranging from 1 to 6. It is preferred that n be 1 to 4. The carbon chains which "n" represents may be either linear or branched.

Partial List of Such Compounds of General Formula (I) is as Follows:

11-(2-N,N-Dimethylaminoethyl)-6H-isoindolo[2,1-a]indole;

2-Chloro-11-(2-N,N-dimethylaminoethyl)-6H-isoindolo[2,1-a]indole;

2-Chloro-11-(2-N,N-dimethylaminoethyl)-6H-isoindolo[2,1-a]indole hydrochloride salt;

2-Chloro-11-(2-N,N-dimethylaminoethyl)-6H-isoindolo[2,1-a]indole maleic acid salt;

2-Chloro-11-(2-N,N-dimethylaminoethyl)-6H-isoindolo[2,1-a]indole D,L-malic acid salt;

2-Chloro-11-(2-N,N-dimethylaminoethyl)-6H-isoindolo[2,1-a]indole oxalate salt;

2-Chloro-11-(2-N,N-dimethylaminoethyl)-6H-isoindolo[2,1-a]indole citrate salt;

2-Fluoro-11-(2-N,N-dimethylaminoethyl)-6H-isoindolo[2,1-a]indole;
2-Chloro-11-(2-N,N-diethylaminoethyl)-6H-isoindolo[2,1-a]indole citrate salt;
2-Fluoro-11-(2-N,N-diethylaminoethyl)-6H-isoindolo[2,1-a]indole;
2-Chloro-11-(2-N-cyclopropyl-N-methylaminoethyl)-6H-isoindolo[2,1-a]indole citrate salt;
2-Fluoro-11-(2-N-cyclopropyl-N-methylaminoethyl)-6H-isoindolo[2,1-a]indole;
11-(2-N,N-Dimethylaminoethyl)-2-methyl-6H-isoindolo[2,1-a]indole;
11-(2-N,N-Dimethylaminoethyl)-2-methoxy-6H-isoindolo[2,1-a]indole;
2-Bromo-11-(2-N,N-diethylaminoethyl)-6H-isoindolo[2,1-a]indole;
2-Bromo-11-(2-N-methyl-N-cyclopropylaminoethyl)-6H-isoindolo[2,1-a]indole;
4-Chloro-11-(2-N,N-dimethylaminoethyl)-6H-isoindolo[2,1-a]indole;
3,4-Dichloro-11-(2-N,N-dimethylaminoethyl)-6H-isoindolo[2,1-a]indole;
1-Chloro-11-(2-N,N-dimethylaminoethyl)-4methyl-6H-isoindolo[2,1-a]indole;
3-Chloro-11-(2-N,N-dimethylaminoethyl)-4methyl-6H-isoindolo[2,1-a]indole;
3-Chloro-11-[(2-N-methylamino)ethyl]-4-methyl-6H-isoindolo[2,1-a]indole;
2-Bromo-11-(2-N,N-diethylaminoethyl)-6H-isoindolo[2,1-a]indole;
2-Bromo-11-(2-N-methyl-N-cyclopropylaminoethyl)-6H-isoindolo[2,1-a]indole;
4-Chloro-11-(2-N,N-dimethylaminoethyl)-6H-isoindolo[2,1-a]indole;
3,4-Dichloro-11-(2-N,N-dimethylaminoethyl)-6H-isoindolo[2,1-a]indole;
1-Chloro-11-(2-N,N-dimethylaminoethyl)-4methyl-6H-isoindolo[2,1-a]indole;
3-Chloro-11-(2-N,N-dimethylaminoethyl)-4-methyl-6H-isoindolo[2,1-a]indole;
3-Chloro-11-[(2-N,N-diacetylamino)ethyl]-4-methyl-6H-isoindolo[2,1-a]indole;
3-Chloro-11-[(2-N-acetylamino)ethyl]-4-methyl-6H-isoindolo[2,1-a]indole;
3-Chloro-11-[(2-N-acetylamino)ethyl]-2-methoxy-6H-isoindolo[2,1-a]indole;
3-Chloro-11-[(2-N-acetylamino)ethyl]-2-sulfoamido-6H-isoindolo[2,1-a]indole;
3-Iodo-11-[(2-N-acetylamino)ethyl]-2-methoxy-6H-isoindolo[2,1-a]indole;
3-Chloro-11-[(2-N-methylamino)ethyl]-4-methyl-6H-isoindolo[2,1-a]indole;
3-Chloro-11-[(2-N-methyl-N-acetylamino)ethyl]-4methyl-6H-isoindolo[2,1-a]indole;
3-Chloro-11-[(2-N-methylamino)ethyl]-2-methoxy-6H-isoindolo[2,1-a]indole;
3-Chloro-11-[(2-N-methylamino)ethyl]-2-sulfoamido-6H-isoindolo[2,1-a]indole;
3-Iodo-11-[(2-N-methylamino)ethyl]-2-methoxy-6H-isoindolo[2,1-a]indole;
11-(2-N,N-Dimethylaminoethyl)-4-trifluoromethyl-6H-isoindolo[2,1-a]indole;
2,4-Difluoro-11-(2-N,N-dimethylaminoethyl)-6H-isoindolo[2,1-a]indole;
11-(2-Pyrrolidin-1-ylethyl)-6H-isoindolo[2,1-a]indole;
2-Bromo-11-(2-pyrrolidin-1-ylethyl)-6H-isoindolo[2,1-a]indole;
11-(2-(Piperidin-1-yl)ethyl)-6H-isoindolo[2,1-a]indole;
11-(2-(4-Methylpiperazin-1-yl)ethyl)-6H-isoindolo[2,1-a]indole;
11-(3-(Pyrrolidin-1-yl)-1-hydroxyprop-1-yl)-6H-isoindolo[2,1-a]indole;
2-Bromo-11-(3-(piperidin-1-yl)-1-hydroxyprop-1-yl)-6H-isoindolo[2,1-a]indole;
11-(2-N,N-Dimethylaminoethyl)-4-ethyl-6H-isoindolo[2,1-a]indole;
11-(2-N,N-Dimethylamino-1-hydroxyethyl)-6H-isoindolo[2,1-a]indole;
11-(2-N,N-Dimethylaminoethyl)-4-methoxy-6H-isoindolo[2,1-a]indole;
2-Bromo-11-(2-N,N-dimethylaminoethyl)-6H-isoindolo[2,1-a]indole;
4-Bromo-11-(2-N,N-dimethylaminoethyl)-6H-isoindolo[2,1-a]indole;
4-Fluoro-11-(2-N,N-dimethylaminoethyl)-6H-isoindolo[2,1-a]indole;
2-Bromo-11-(2-(4-methylpiperazin-1-yl)ethyl)-6H-isoindolo[2,1-a]indole;

and its stereoisomers, its N-oxides, its polymorphs, its pharmaceutically acceptable salts and solvates.

The present invention also envisages some useful bioactive metabolites of the compounds of general formula (I).

The compounds of general formula (I) of this invention are useful in the treatment and/or prophylaxis of a condition wherein modulation of 5-HT activity is desired.

The compounds of general formula (I) of this invention are useful in the treatment and/or prophylaxis of a condition wherein modulation of 5-HT and melatonin activities gives desired effect.

The present invention provides for use of the compounds of general formula (I) according to above, for the manufacture of the medicaments for the potential use in the treatment and/or prophylaxis of certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficit Disorder/Hyperactivity Syndrome), personality disorders, psychosis, paraphrenia, psychotic depression, mania, schizophrenia, schizophreniform disorders, withdrawal from drug abuse such as cocaine, ethanol, nicotine and benzodiazepines, panic attacks, reproduction, glaucoma, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The compounds of the invention are also expected to be of use in the treatment of certain GI (Gastrointestinal) disorders such as IBS (irritable bowel syndrome) or chemotherapy induced emesis.

The compounds of the invention are also expected to be of use in the modulation of eating behavior and these compounds can also be used to reduce morbidity and mortality associated with the excess weight.

The present invention provides a method for the treatment of a human or a animal subject suffering from certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficit Hyperactivity Disorder), personality disorders, psychosis, paraphrenia, psychotic depression, mania, schizophrenia, schizophreniform disorders, withdrawal from drug abuse such as cocaine, ethanol, nicotine and benzodiazepines, panic attacks, reproduction, glaucoma, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The present invention also provides a method for modulating 5-HT and/or melatonin receptor function desired in certain cases.

The present invention also includes a isotopically-labelled compounds, which are identical to those defined in the general formula (I), but for the fact that one or more atoms are replaced by an atom having an atomic mass or mass number different from the atomic mass or mass number found usually in nature. Examples of isotopes that can be incorporated into compounds of the invention include isotopes of hydrogen, carbon, nitrogen, oxygen, phosphorus, fluorine, chlorine, iodine, bromine and mTecnitium, exemplified by $^2H$, $^3H$, $^{11}C$, $^{13}C$, $^{14}C$, $^{13}N$, $^{15}N$, $^{15}O$, $^{18}F$, $^{99m}Tc$, $^{31}P$, $S$, $^{123}I$ and $^{125}I$. Compounds of present invention and pharmaceutically acceptable salts and prodrugs of said compounds that contain the aforementioned isotopes and/or other isotopes of other atoms are within the scope of this invention.

Isotopically labelled compounds of the present invention are useful in drug and/or substrate tissue distribution and target occupancy assays. For example, isotopically labelled compounds are particularly useful in SPECT (single photon emission computed tomography) and in PET (positron emission tomography).

An effective amount of a compound of general formula (I) or its salt is used for producing medicaments of the present invention, along with conventional pharmaceutical auxiliaries, carriers and additives.

The present invention also relates to a pharmaceutical composition for treating and/or prophylaxis of disorders, a condition wherein modulation of 5-HT is desired in a mammal, comprising:
   a. a pharmaceutically acceptable carrier
   b. a compound of general formula (I) as defined above, and
   c. a 5-HT re-uptake inhibitor, or its pharmaceutically acceptable salt;
wherein the amounts of each active compound (a compound of general formula (I) and a 5-HT re-uptake inhibitor), is such that the combination is effective in treating such a condition.

The present invention also relates to a method of treatment and/or prophylaxis of disorders, a condition wherein modulation of 5-HT is desired in a mammal, comprising:
   a. a pharmaceutically acceptable carrier
   b. a compound of general formula (I) as defined above, and
   c. a 5-HT re-uptake inhibitor, or its pharmaceutically acceptable salt;
wherein the amounts of each active compound (a compound of general formula (I) and a 5-HT re-uptake inhibitor), is such that the combination is effective in treating such a condition.

The present invention also relates to a pharmaceutical composition for treating and/or prophylaxis of disorders, a condition wherein modulation of 5-HT and/or melatonin is desired in a mammal, comprising:
   a. a pharmaceutically acceptable carrier
   b. a compound of general formula (I) as defined above, and
   c. a serotonergic or melatonergic ligand, or its pharmaceutically acceptable salt;
wherein the amounts of each active compound (a compound of general formula (I) and a serotonergic ligand), is such that the combination is effective in treating such a condition.

The present invention also relates to a method of treatment and/or prophylaxis of disorders, a condition wherein modulation of 5-HT and/or melatonin is desired in a mammal, comprising:
   a. a pharmaceutically acceptable carrier
   b. a compound of general formula (I) as defined above, and
   c. either of a serotonergic or melatonergic ligand, or its pharmaceutically acceptable salt;
wherein the amounts of each active compound (a compound of general formula (I) and a serotonergic or melatonergic ligand), is such that the combination is effective in treating such a condition.

The present invention also relates to a process for the preparation of the above said novel compounds, their derivatives, their analogues, their tautomeric forms, their stereoisomers, their geometric forms, their N-oxides, their polymorphs, their pharmaceutically acceptable salts, their pharmaceutically acceptable solvates, novel intermediates described herein and pharmaceutical compositions containing them.

DETAILED DESCRIPTION OF THE INVENTION

The present invention relates to novel tetracyclic arylalkyl, their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them.

More particularly, the present invention relates to novel tetracyclic arylalkyl of the general formula (I), their derivatives, their analogs, their tautomeric forms, their stereoisomers, their polymorphs, their pharmaceutically acceptable salts, their pharmaceutically acceptable solvates, novel intermediates described herein and pharmaceutically acceptable compositions containing them and use of these compounds in medicine.

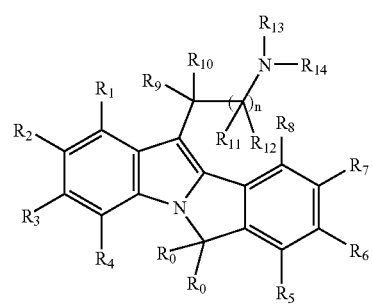

General formula (I)

wherein $R_0$ is either hydrogen or linear or branched $(C_1\text{-}C_2)$ alkyl;

$R_1$, $R_2$, $R_3$, $R_4$, $R_5$, $R_6$, $R_7$, $R_8$, $R_9$, $R_{10}$, $R_{11}$, and $R_{12}$ may be same or different and each independently represent hydrogen, halogen, perhaloalkyl, amino, unsubstituted groups such as linear or branched $(C_1\text{-}C_{12})$alkyl, $(C_3\text{-}C_7)$cycloalkyl, $(C_1\text{-}C_{12})$alkoxy, cyclo$(C_3\text{-}C_7)$alkoxy, aryl, aryloxy, aralkyl, aralkoxy, heterocyclyl, heteroaralkyl, acyl, acyloxy, acylamino, monoalkylamino, dialkylamino, arylamino, diarylamino, aralkylamino, hydroxyalkyl, aminoalkyl, monoalkylaminoalkyl, dialkylaminoalkyl, alkoxyalkyl, alkylthio, thioalkyl, aminocarbonylamino, dialkylaminocarbonylamino, carboxylic acid and its derivatives.

$R_{13}$ and $R_{14}$ may be same or different and each independently represents hydrogen, substituted or unsubstituted groups such as linear or branched $(C_1\text{-}C_4)$alkyl, $(C_3\text{-}C_7)$ cycloalkyl, $(C_3\text{-}C_7)$cycloalkenyl, bicycloalkyl, bicycloalkenyl, aryl, aralkyl, optionally $R_{13}$ and $R_{14}$ along with the nitrogen atom, may form a 3, 4, 5, 6 or 7-membered heterocyclic ring, wherein the ring may be further substituted, and it may have either one, two or three double bonds or "additional heteroatoms", as defined above.

"n" is an integer ranging from 1 to 6. It is preferred that n be 1 to 4. The carbon chains which "n" represents may be either linear or branched.

Suitable groups represented by $R_1$, $R_2$, $R_3$, $R_4$, $R_5$, $R_6$, $R_7$, $R_8$, $R_9$, $R_{10}$, $R_{11}$, and $R_{12}$ may be a halogen atom such as fluorine, chlorine, bromine or iodine; perhaloalkyl particularly perhalo$(C_1\text{-}C_6)$alkyl such as fluoromethyl, difluoromethyl, trifluoromethyl, trifluoroethyl, fluoroethyl, difluoroethyl and the like; substituted or unsubstituted $(C_1\text{-}C_{12})$alkyl group, linear or branched $(C_1\text{-}C_8)$alkyl group, such as methyl, ethyl, n-propyl, iso-propyl, n-butyl, iso-butyl, t-butyl, n-pentyl, iso-pentyl, hexyl, iso-hexyl, heptyl, octyl and the like; cyclo$(C_3\text{-}C_7)$alkyl group such as cyclopropyl, cyclobutyl, cyclopentyl, cyclohexyl, cycloheptyl, the cycloalkyl group may be substituted; $(C_1\text{-}C_{12})$alkoxy, especially, $(C_1\text{-}C_6)$alkoxy group such as methoxy, ethoxy, propyloxy, butyloxy, iso-propyloxy and the like, which may be substituted; cyclo$(C_3\text{-}C_7)$ alkoxy group such as cyclopropyloxy, cyclobutyloxy, cyclopentyloxy, cyclohexyloxy, cycloheptyloxy and the like, the cycloalkoxy group may be substituted; aryl group such as phenyl or naphthyl, the aryl group may be substituted; aralkyl group such as benzyl, phenethyl, $C_6H_5CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, imidazolyl, oxadiazolyl, tetrazolyl, benzopyranyl, beniofuranyl and the like, the heteroaryl group may be substituted; heterocyclo$(C_1\text{-}C_6)$alkyl, such as pyrrolidinylalkyl, piperidinylalkyl, morpholinylalkyl, thiomorpholinylalkyl, oxazolinylalkyl and the like, the heterocyclo$(C_1\text{-}C_6)$alkyl group may be substituted; heteroaralkyl group such as furanylmethyl, pyridinylmethyl, oxazolylmethyl, oxazolylethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be substituted; acyl groups such as acetyl, propionyl or benzoyl, the acyl group may be substituted; acyloxy group such as $CH_3COO$, $CH_3CH_2COO$, $C_6H_5COO$ and the like which may optionally be substituted, acylamino group such as $CH_3CONH$, $CH_3CH_2CONH$, $C_3H_7CONH$, $C_6H_5CONH$ which may be substituted, $(C_1\text{-}C_6)$monoalkylamino group such as $CH_3NH$, $C_2H_5NH$, $C_3H_7NH$, $C_6H_{13}NH$ and the like, which may be substituted, $(C_1\text{-}C_6)$dialkylamino group such as $N(CH_3)_2$, $CH_3(C_2H_5)N$ and the like, which may be substituted; arylamino group such as $C_6H_5NH$, $CH_3(C_6H_5)N$, $C_6H_4(CH_3)NH$, $NH\text{—}C_6H_4\text{-Hal}$ and the like, which may be substituted; arylalkylamino group such as $C_6H_5CH_2NH$, $C_6H_5CH_2CH_2NH$, $C_6H_5CH_2NCH_3$ and the like, which may be substituted; hydroxy$(C_1\text{-}C_6)$alkyl which may be substituted, amino$(C_1\text{-}C_6)$alkyl which may be substituted; mono $(C_1\text{-}C_6)$alkylamino$(C_1\text{-}C_6)$alkyl, di$(C_1\text{-}C_6)$alkylamino$(C_1\text{-}C_6)$alkyl group which may be substituted, alkoxyalkyl group such as methoxymethyl, ethoxymethyl, methoxyethyl, ethoxyethyl and the like, which may be substituted; aminocarbonylamino group; $(C_1\text{-}C_6)$alkylaminocarbonylamino group, di$(C_1\text{-}C_6)$alkylaminocarbonylamino group; carboxylic acid or its derivatives such as amides, like $CONH_2$, alkylaminocarbonyl like $CH_3NHCO$, $(CH_3)_2NCO$, $C_2H_5NHCO$, $(C_2H_5)_2NCO$, arylaminocarbonyl like PhNHCO, NapthylNHCO and the like, aralkylaminocarbonyl such as $PhCH_2NHCO$, $PhCH_2CH_2NHCO$ and the like, heteroarylaminocarbonyl and heteroaralkylamino carbonyl groups where the heteroaryl groups are as defined earlier, heterocyclylaminocarbonyl where the heterocyclyl group is as defined earlier, carboxylic acid derivatives such as esters, wherein the ester moieties are alkoxycarbonyl groups such as unsubstituted or substituted phenoxycarbonyl, naphthyloxycarbonyl and the like; aralkoxycarbonyl group such as benzyloxycarbonyl, phenethyloxycarbonyl, naphthylmethoxycarbonyl and the like, heteroaryloxycarbonyl, heteroaralkoxycarbonyl, wherein the heteroaryl group is as defined earlier, heterocyclyoxycarbonyl where heterocycle is as defined earlier and these carboxylic acid derivatives may be substituted;

$R_{13}$ and $R_{14}$ represents hydrogen, substituted or unsubstituted linear or branched $(C_1\text{-}C_{12})$alkyl such as methyl, ethyl, n-propyl, iso-propyl, n-butyl, iso-butyl, pentyl, hexyl, octyl and the like; aryl group such as phenyl or naphthyl, the aryl group may be substituted; cyclo$(C_3\text{-}C_7)$alkyl group such as cyclopropyl, cyclobutyl, cyclopentyl, cyclohexyl, cycloheptyl, the cycloalkyl group may be substituted; Suitable hetero cyclic rings formed between $R_{13}$ and $R_{14}$ along with "Nitrogen atom" be such as pyrrolyl, pyrrolidinyl, pipeddinyl, pyridinyl, 1,2,3,4-Tetrahydro-pyridinyl, imidazolyl, pyrimidinyl, pyrazinyl, piperazinyl, diazolinyl and the like; the heterocyclyl group may be substituted; heteroaryl group such as pyridyl, imidazolyl, tetrazolyl and the like, the heteroaryl group may be substituted; heterocyclo$(C_1\text{-}C_6)$ alkyl, such as pyrrolidinealkyl, piperidinealkyl, morpholinealkyl, thiomorpholinealkyl, oxazolinealkyl and the like, the heterocyclo$(C_1\text{-}C_6)$alkyl group may be substituted; heteroaralkyl group such as furanmethyl, pyridinemethyl, oxazolemethyl, oxazolethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be further substituted.

In the case of the compounds of general formula (I) having an asymmetric carbon atom the present invention relates to the D-form, the L-form and D,L-mixtures and in the case of a number of asymmetric carbon atoms, the diastereomeric forms and the invention extends to each of these stereoisomeric forms and to mixtures thereof including racemates. Those compounds of general formula (I) which have an asymmetric carbon and as a rule are obtained as racemates can be separated one from the other by the usual methods, or any given isomer may be obtained by stereospecific or asymmetric synthesis. However, it is also possible to employ an optically active compound from the start, a correspondingly optically active or diastereomeric compound then being obtained as the final compound.

In the case of the compounds of general formula (I), where tautomerism may exist, the present invention relates to all of the possible tautomeric forms and the possible mixture thereof.

In the case of the compounds of general formula (I) containing geometric isomerism the present invention relates to all of these geometric isomers.

Suitable pharmaceutically acceptable acid addition salts of compounds of the general formula (I) can be prepared of the aforementioned base compounds of this invention are those which form non-toxic acid addition salts, includes, salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benezenesulfonate, p-toluenesulfonate, palmoate and oxalate.

Suitable pharmaceutically acceptable base addition salts of compounds of the general formula (I) can be prepared of the aforementioned acid compounds of this invention are those which form non-toxic base addition salts, includes, salts containing pharmaceutically acceptable cations, such as lithium, sodium, potassium, calcium and magnesium, salts of organic bases such as lysine, arginine, guanidine, diethanolamine, choline, tromethamine and the like; ammonium or substituted ammonium salts.

Pharmaceutically acceptable salts forming part of this invention are intended to define but not limited to the above list In addition, pharmaceutically acceptable salts of the compound of formula (I) can be obtained by converting derivatives which have tertiary amino groups into the corresponding quartemary ammonium salts in the methods known in the literature by using quartemizing agents. Possible quartemizing agents are, for example, alkyl halides such as methyl iodide, ethyl bromide and n-propyl chloride, including arylalkyl halides such as benzyl chloride or 2-phenylethyl bromide.

In the addition to pharmaceutically acceptable salts, other salts are included in the invention. They may serve as intermediates in the purification of the compounds, in the preparation of other salts, or in the identification and characterization of the compounds or intermediates.

The pharmaceutically acceptable salts of compounds of formula (I) may exists as solvates, such as with water, methanol, ethanol, dimethylformamide, ethyl acetate, and the like. Mixtures of such solvates can also be prepared. The source of such solvate can be from the solvent of crystallization, inherent in the solvent preparation or crystallization, or adventitious to such solvent. Such solvates are within the scope of this invention.

The invention also encompasses the pharmaceutically acceptable prodrugs of the compounds of the formula (I). A prodrug is a drug which has been chemically modified and may be biologically in-active at the site of action, but which may be degraded or modified by one or more enzymatic or other in-vivo processes to the parent form. This prodrug should have a different pharmacokinetic profile than the parent, enabling easier absorption across the mucosal epithelium, better salt formation, or solubility, and/or improved systemic stability (an increase in the plasma half-life, for example). Typically, such chemical modifications include the following:

1. ester or amide derivatives which may be cleaved by esterases or lipases;
2. peptides which may be recognized by specific or non-specific proteases; or
3. derivatives that accumulate at a site of action through membrane selection of a prodrug from or a modified prodrug form; or any combination of 1 to 3, above.

Conventional procedures for the selection and preparation of suitable prodrug derivatives are described, for example, in H. Bundgard, Design of prodrugs, (1985).

Compounds of general formula (I) can be prepared by any of the methods described below. The present invention also provides processes for preparing compounds of general formula (I) as defined above, their derivatives, their analogs, their tautomeric forms, their stereoisomers, their geometric forms, their polymorphs, their pharmaceutically acceptable salts and their pharmaceutically acceptable solvates, novel intermediates described herein, where $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and "n" are as defined previously can be prepared by any of the methods described below:

Scheme-1:

Compounds of general formula (I), may be prepared by cyclizing a novel intermediate of formula (II) given below,

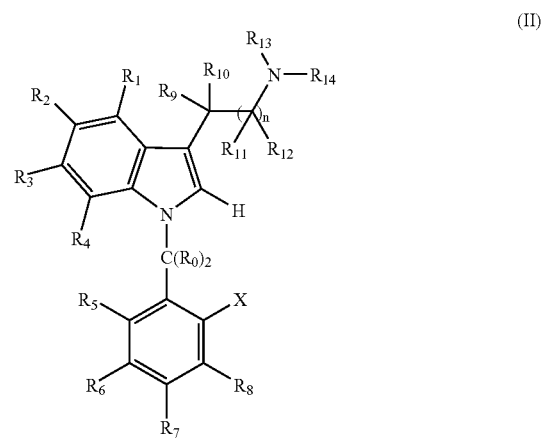

wherein X is halogen such chloro, bromo or iodo, $R_0$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and "n" are as defined previously, using a Pd(0) or Pd (II) derivative as a catalyst, for example tetrakis triphenylphosphine palladium, (Bis-tri-o-tolylphosphine) palladium and the like; and thereafter if necessary:

i) converting a compound of the formula (I) into another compound of the formula (I); and/or
ii) removing any protecting groups; and/or
iii) forming a pharmaceutically acceptable salt, solvate, polymorph or prodrug thereof.

This cyclization reaction can be achieved using variety of palladium catalysts. The reaction may be affected in the presence of a base such as $CH_3COOK$. This reaction may be carried out in the presence of solvents such as THF, DMF, DMSO, DMA, DME, acetone and the like and preferably using Dimethylacetamide. The inert atmosphere may be maintained by using inert gases such as $N_2$, Ar or He. The reaction temperature may range from 50° C. to 200° C. based on the choice of solvent and preferably at a temperature of 160° C. The duration of the reaction may range from 1 to 24 hours, preferably from 10 to 20 hours.

Scheme-2:

Compounds of general formula (I), may be prepared by reacting a compound of formula (III) given below,

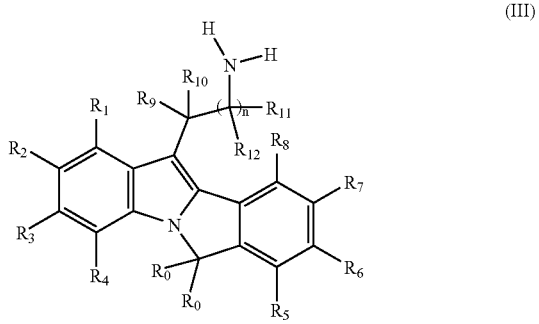

(III)

wherein $R^0$, $R^1$, $R_2$, $R_3$, $R_4$, $R_5$, $R_6$, $R_7$, $R_8$, $R_9$, $R_{10}$, $R^{11}$, $R_{12}$ and "n" are as defined previously, with a suitable alkylating agent such as $R_{13}X$ or $R_{14}X$ or $XR_{13}R_{14}X$ in successive steps or in one step, wherein X is good leaving group such as halogen, hydroxyl and the like; and thereafter if desired or necessary carrying out steps (i), (ii) and/or (iii) as described above.

The reaction is preferably carried in an organic solvent inert to the conditions of the reaction, such as acetone, THF or DMF and the like or mixtures thereof. The inert atmosphere may be maintained by using inert gases such as $N_2$, Ar or He. The reaction may be affected in the presence of a base such as $K_2CO_3$, $Na_2CO_3$, TEA or mixtures thereof. The reaction temperature may range from 20° C. to 200° C. based on the solvent employed and preferably at a temperature in the range from 30° C. to 150° C. The duration of the reaction may range from 1 to 24 hours, preferably from 2 to 6 hours.

Scheme-3:

Compounds of general formula (I), may be prepared by reacting a compound of formula (IV) given below,

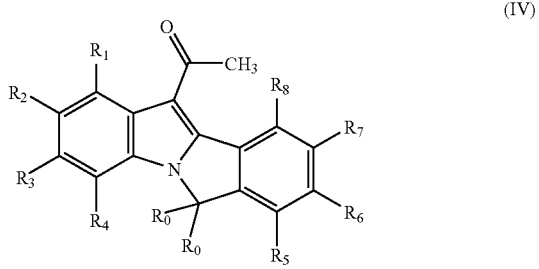

(IV)

wherein $R_0$, $R_1$, $R_2$, $R_3$, $R_4$, $R_5$, $R_6$, $R_7$, $R_8$ and "n" are as defined previously, with formaldehyde and a compound of formula (V) given below, $NHR_{13}R_{14}$ (V)

wherein $R_{13}$ and $R_{14}$ are as defined earlier; and thereafter if desired or necessary carrying out steps (i), (ii) and/or (iii) as described above.

The above reaction is preferably carried out at a temperature of 50° C. to 150° C. The formaldehyde can be in the form of as aqueous solution i.e. 40% formalin solution, or a polymeric form of formaldehyde such as paraformaldehyde or trioxymethylene. When such polymeric forms are used, a molar excess of mineral acid, for example hydrochloric acid, is added to regenerate the free aldehyde from the polymer. The reaction is preferably carried in an organic solvent inert to the conditions of the reaction, such as methanol, ethanol or 3-methylbutanol and the like or a mixture thereof, and preferably using either acetone or DMF. The inert atmosphere may be maintained by using inert gases such as $N_2$, Ar or He. The reaction temperature may range from 20° C. to 150° C. based on the choice of solvent and preferably at a temperature in the range from 30° C. to 100° C. The duration of the reaction may range from 1 to 24 hours, preferably from 2 to 6 hours.

Scheme-4:

Compounds of general formula (I), may be prepared from another compound of formula (I) containing —C(=O) group/s in the side chain, by known methods of reduction to the corresponding —C(OH,H) or —C(H,H) compound; and thereafter if desired or necessary carrying out steps (i), (ii) and/or (iii), as described above.

Novel intermediates of general formula (IV) are represented as given below,

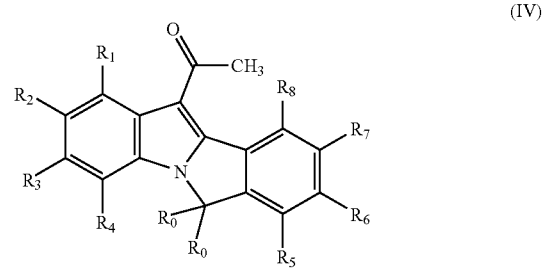

(IV)

wherein $R_0$, $R_1$, $R_2$, $R_3$, $R_4$, $R_5$, $R_6$, $R_7$, $R_8$ and 'n' are as defined previously.

The present invention also provides method to prepare intermediate of general formula (IV), which comprises of cyclizing compounds of formula (VIII),

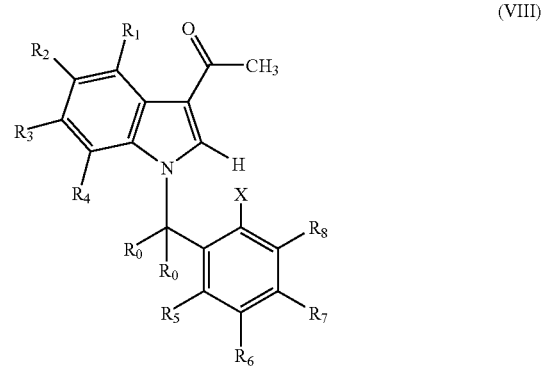

(VIII)

wherein $R_1$, $R_2$, $R_3$, $R_4$, $R_5$, $R_6$, $R_7$ and $R_8$ are as defined above; using a Pd(0) or Pd (II) derivative as a catalyst, for example tetrakis triphenylphosphine palladium, (Bis-tri-o-tolylphosphine) palladium and the like in a suitable solvent.

During any of the above synthetic sequences it may be necessary and/or desirable to protect sensitive or reactive groups on any of the molecules concerned. This may be achieved by means of conventional protecting groups, such as those described in Protective Groups in Organic Chemistry, Ed J. F. W. McOmie, Plenum Press, 1973; and T. W. Greene & P. G. M. Wuts, Protective Groups in Organic Synthesis, John Wiley & Sons, 1991. For example, suitable protecting groups for the piperazine group include BOC, $COCCl_3$, $COCF_3$. The protecting groups may be removed according to the standard procedures.

The protecting groups may be removed at a convenient subsequent stage using methods known from the art.

The compounds of the present invention may contain one or more asymmetric centers and therefore they also exist as stereoisomers. The stereoisomers of the compounds of the present invention may be prepared by one or more ways presented below:

i) One or more of the reagents may be used in their optically active form.

ii) Optically pure catalyst or chiral ligands along with metal catalyst may be employed in the reduction process. The metal catalyst may be Rhodium, Ruthenium, indium and the like. The chiral ligands may preferably be chiral phosphines (Principles of Asymmetric synthesis, J. E. Baldwin Ed., Tetrahedron series, 14, 311-316).

iii) The mixture of stereoisomers may be resolved by conventional methods such as forming a diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amine acids and the like. Chiral bases that can be employed may be cinchona alkaloids, brucine or a basic amino acid such as lysine, arginine and the like.

The pharmaceutically acceptable salts forming a part of this invention may be prepared by treating the compound of formula (I) with 1-6 equivalents of a base such as Lithium, ammonia, substituted ammonia, sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used. Organic bases such lysine, arginine, methyl benzylamine, ethanolamine, diethanolamine, tromethamine, choline, guanidine and their derivatives may be used. Acid addition salts, wherever applicable may be prepared by treatment with acids such as tartaric acid, mandelic acid, fumaric acid, maleic acid, lactic acid, salicyclic acid, citric acid, ascorbic acid, benzene sulfonic acid, p-toluene sulfonic acid, hydroxynaphthoic acid, methane sulfonic acid, malic acid, acetic acid, benzoic acid, succinic acid, palmitic acid, oxalic acid, hydrochloric acid, hydrobromic acid, sulfuric acid, nitric acid and the like in solvents such as water, alcohols, ethers, ethyl acetate, dioxane, DMF or a lower alkyl ketone such as acetone, or the mixtures thereof.

Different polymorphs may be prepared by crystallization of compounds of general formula (I) under different conditions such as different solvents or solvent mixtures in varying proportions for recrystallization, various ways of crystallization such as slow cooling, fast cooling or a very fast cooling or a gradual cooling during crystallization. Different polymorphs may also be obtained by heating the compound, melting the compound and solidification by gradual or fast cooling, heating or melting under vacuum or under inert atmosphere and cooling under either vacuum or inert atmosphere. The various polymorphs may be identified by either one or more of the following techniques such as differential scanning calorimeter, powder X-ray diffraction, IR spectroscopy, solid probe NMR spectroscopy and thermal microscopy.

Another aspect of the present invention comprises of a pharmaceutical composition, containing at least one of the compounds of the general formula (I), their derivatives, their analogs, their derivatives, their tautomeric forms, their stereoisomers, their geometric forms, their polymorphs, their pharmaceutically acceptable salts, their pharmaceutically acceptable solvates thereof as an active ingredient, together with pharmaceutically employed carriers, auxiliaries and the like.

The pharmaceutical compositions of the present invention may be formulated in a conventional manner using one or more pharmaceutically acceptable carriers. Thus, the active compounds of the invention may be formulated for oral, buccal, intranasal, parental (e.g., intravenous, intramuscular or subcutaneous) or rectal administration or a form suitable for administration by inhalation or insulation.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion.

Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer, or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule it preferably should be in the form of powder. Capsules and cartridges (made, for example, from gelatin) for use in an inhaler or insufflator may be formulated containing a powder mix of a compound of the invention and a suitable powder base such as lactose or starch.

A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

The affinities of the compound of this invention for the various serotonin receptors are evaluated using standard radioligand binding assays and are described here.

Radioligand Binding Assays for Various 5-ht Receptor Subtypes:

i) Assay for $5HT_{1A}$

Materials and Methods:
Receptor source: Human recombinant expressed in HEK-293 cells
Radioligand: [3H]-8-OH-DPAT (221 Ci/mmol)
Final ligand concentration—[0.5 nM]
Reference compound: 8-OH-DPAT
Positive control: 8-OH-DPAT Incubation Conditions:
Reactions are carried out in 50 mM TRIS-HCl (pH 7.4) containing 10 mM $MgSO_4$, 0.5 mM EDTA and 0.1% Ascorbic acid at room temperature for 1 hour. The reaction is terminated by rapid vacuum filtration onto glass fiber filters. Radioactivity trapped onto the filters is determined and compared to control values in order to ascertain any interactions of test compound with the $5HT_{1A}$ binding site.

Literature Reference

Hoyer D., Engel G., et al. Molecular Pharmacology of $5HT_1$ and $5-HT_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. Eur. Jrnl. Pharmacol. 118: 13-23 (1985) with modifications.

Schoeffter P. and Hoyer D. How Selective is GR 43175? Interactions with Functional $5-HT_{1A}$, $5HT_{1B}$, $5-HT_{1C}$, and $5-HT_{1D}$ Receptors. Naunyn-Schmiedeberg's Arch. Pharmac. 340: 135-138 (1989) with modifications.

ii) Assay for $5HT_{1B}$

Materials and Methods:
Receptor source: Rat striatal membranes
Radioligand: [$^{125}$I]Iodocyanopindolol (2200 Ci/mmol)
Final ligand concentration—[0.15 nM]
Non-specific determinant: Serotonin—[10 μM]
Reference compound: Serotonin
Positive control: Serotonin Incubation Conditions:
Reactions are carried out in 50 mM TRIS-HCl (pH 7.4) containing 60 μM (−) isoproterenol at 37° C. for 60 minutes. The reaction is terminated by rapid vacuum filtration onto glass fiber filters. Radioactivity trapped onto the filters is determined and compared to control values in order to ascertain any interactions of test compound with the $5HT_{1B}$ binding site.

LITERATURE REFERENCE

Hoyer D., Engel G., et al. Molecular Pharmacology of $5HT_1$ and $5-HT_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. *Eur. Jrnl. Pharmacol.* 118: 13-23 (1985) with modifications.

Schoeffter P. and Hoyer D. How selective is GR 43175? Interactions with Functional $5-HT_{1A}$, $5HT_{1B}$, $5-HT_{1C}$, and $5-HT_1$ Receptors. *Naunyn-Schmiedeberg's Arch. Pharmac.* 340: 135-138 (1989) with modifications.

iii) Assay for $5HT_{1D}$

Materials and Methods:
Receptor source: Human cortex
Radioligand: [$^3$H] 5-Carboxamidotryptamine (20-70 Ci/mmol)
Final ligand concentration—[2.0 nM]
Non-specific determinant: 5-Carboxamidotryptamine (5-CT)—[1.0 μM]
Reference compound: 5-Carboxamidotryptamine (5-CT)
Positive control: 5-Carboxamidotryptamine (5-CT)

Incubation Conditions:
Reactions are carried out in 50 mM TRIS-HCl (pH 7.7) containing 4 mM $CaCl_2$, 100 nM 8-OH-DPAT, 100 nM Mesulergine, 10 uM Pargyline and 0.1% ascorbic acid at 25° C. for 60 minutes. The reaction is terminated by rapid vacuum filtration onto glass fiber filters. Radioactivity trapped onto the filters is determined and compared to control values in order to ascertain any interactions of test compound with the cloned $5HT_{1D}$ binding site.

Literature Reference:
Waeber C., Schoeffter, Palacios J. M. and Hoyer D. Molecular Pharmacology of the $5-HT_{1D}$ Recognition Sites: Radioligand Binding Studies in Human, Pig, and Calf Brain Membranes. Naunyn-Schmiedeberg's Arch. Pharmacol. 337: 595-601 (1988) with modifications.

iv) Assay for $5HT_{2A}$

Materials and Methods:
  Receptor source: Human Cortex
  Radioligand: [$^3$H] Ketanserin (60-90 Ci/mmol)
  Final ligand concentration—[2.0 nM]
  Non-specific determinant: Ketanserin—[3.0 µM]
  Reference compound: Ketanserin
  Positive control: Ketanserin Incubation Conditions:
Reactions are carried out in 50 mM TRIS-HCl (pH 7.5) at room temperature for 90 minutes. The reaction is terminated by rapid vacuum filtration onto glass fiber filters. Radioactivity trapped onto the filters is determined and compared to control values in order to ascertain any interactions of test compound with the $5HT_{2A}$ binding site.

LITERATURE REFERENCE

Leysen J. E., Niemegeers C. J., Van Nueten J. M. and Laduron P. M. [$^3$H]Ketanserin: A Selective Tritiated Ligand for Serotonin$_2$ Receptor Binding Sites. Mol. Pharmacol. 21: 301-314 (1982) with modifications.

Martin, G. R. and Humphrey, P. P. A. Classification Review: Receptors for 5-HT: Current Perspectives on Classification and Nomenclature. Neuropharmacol. 33(3/4): 261-273 (1994).

v) Assay for $5HT_{2C}$

Materials and Methods:
  Receptor source: Pig choroid plexus membranes
  Radioligand : [$^3$H] Mesulergine (50-60 Ci/mmol)
  Final ligand concentration—[1.0 nM]
  Non-specific determinant: Serotonin—[100 µM]
  Reference compound : Mianserin
  Positive control: Mianserin Incubation Conditions:
Reactions are carried out in 50 mM TRIS-HCl (pH 7.7) containing 4 mM CaCl$_2$ and 0.1% ascorbic acid at 37° C. for 60 minutes. The reaction is terminated by rapid vacuum filtration onto glass fiber filters. Radioactivity trapped onto the filters is determined and compared to control values in order to ascertain any interactions of test compound with the $5HT_{2C}$ binding site.

LITERATURE REFERENCE

A. Pazos, D. Hoyer, and J. Palacios. The Binding of Serotonergic Ligands to the Porcine Choroid Plexus: Characterization of a New Type of Serotonin Recognition Site. Eur. Jrnl. Pharmacol. 106: 539-546 (1985) with modifications.

Hoyer, D., Engel, G., et al. Molecular Pharmacology of 5HT$_1$ and 5-HT$_2$ Recognition Sites in Rat and Pig Brain Membranes: Radioligand Binding Studies with [3H]-5HT, [3H]-8-OH-DPAT, [$^{25}$I]-Iodocyanopindolol, [3H]-Mesulergine and [3H]-Ketanserin. Eur. Jrnl. Pharmacol. 118: 13-23 (1985) with modifications.

vi) Assay for $5HT_3$

Materials and Methods:
  Receptor source: N1E-115 cells
  Radioligand: [$^3$H]-GR 65630 (30-70 Ci/mmol)
  Final ligand concentration—[0.35 nM]
  Non-specific determinant: MDL-72222—[1.0 µM]
  Reference compound: MDL-72222
  Positive control: MDL-72222

Incubation Conditions:
Reactions are carried out in 20 mM HEPES (pH 7.4) containing 150 mM NaCl at 25° C. for 60 minutes. The reaction is terminated by rapid vacuum filtration onto glass fiber filters. Radioactivity trapped onto the filters is determined and compared to control values in order to ascertain any interactions of test compound with the $5HT_3$ binding site.

LITERATURE REFERENCE

Lummis S. C. R., Kilpatrick G. J. Characterization of 5HT$_3$ Receptors in Intact N1E-115 Neuroblastoma Cells. Eur. Jrnl. Pharmacol. 189: 223-227 (1990) with modifications.

Hoyer D. and Neijt H. C. Identification of Serotonin 5-HT$_3$ Recognition Sites in Membranes of N1E-115 Neuroblastoma Cells by Radioligand Binding. Mol. Pharmacol. 33: 303 (1988).

Tyers M. B. 5-HT$_3$ Receptors and the Therapeutic Potential of 5HT$_3$ Receptor Antagonists. Therapie. 46:431-435 (1991).

vii) Assay for $5HT_4$

Materials and Methods:
  Receptor source: Guinea pig striatal membranes
  Radioligand: [$^3$H] GR-113808 (30-70 Ci/mmol)
  Final ligand concentration—[0.2 nM]
  Non-specific determinant: Serotonin (5-HT)—[30 µM]
  Reference compound: Serotonin (5-HT)
  Positive control: Serotonin (5-HT)

Incubation Conditions:
Reactions are carried out in 50 mM HEPES (pH 7.4) at 370C for 60 minutes. The reaction is terminated by rapid vacuum filtration onto glass fiber filters. Radioactivity trapped onto the filters is determined and compared to control values in order to ascertain any interactions of test compound with the $5HT_4$ binding site.

LITERATURE REFERENCE

Grossman Kilpatrick, C., et al. Development of a Radioligand Binding Assay for 5HT$_4$ Receptors in Guinea Pig and Rat Brain. Brit. J Pharmco. 109: 618-624 (1993).

viii) Assay for $5HT_{5A}$

Materials and Methods:
  Receptor source: Human recombinant expressed in HEK 293 cells
  Radioligand : [$^3$H] LSD (60-87 Ci/mmol)
  Final ligand concentration—[1.0 nM]
  Non-specific determinant: Methiothepin mesylate—[1.0 µM]
  Reference compound : Methiothepin mesylate
  Positive control: Methiothepin mesylate Incubation Conditions:
Reactions are carried out in 50 mM TRIS-HCl (pH 7.4) containing 10 mM MgSO$_4$ and 0.5 mM EDTA at 37° C. for 60 minutes. The reaction is terminated by rapid vacuum filtration onto glass fiber filters. Radioactivity trapped onto the filters is determined and compared to control values in order to ascertain any interactions of test compound with the cloned $5HT_{5A}$ binding site.

LITERATURE REFERENCE

Rees S., et al. FEBS Letters, 355: 242-246 (1994) with modifications ix) Assay for $5HT_6$ Materials and Methods:

Receptor source: Human recombinant expressed in HEK293 cells
 Radioligand: [$^3$H]LSD (60-80 Ci/mmol)
 Final ligand concentration—[1.5 nM]
 Non-specific determinant: Methiothepin mesylate—[0.1 µM]
  Reference compound: Methiothepin mesylate
  Positive control: Methiothepin mesylate Incubation Conditions:

Reactions are carried out in 50 mM TRIS-HCl (pH 7.4) containing 10 mM $MgCl_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin-$5HT_6$ binding site.

LITERATURE REFERENCE

Monsma F. J. Jr., et al., Molecular Cloning and Expression of Novel Serotonin Receptor with High Affinity for Tricyclic Psychotropic Drugs. Mol. Pharmacol. (43): 320-327 (1993).

x) Assay for 5-$HT_7$

Materials and Methods:

Receptor source : Human recombinant expressed in CHO cells
 Radioligand: [$^3$H]LSD (60-80 Ci/mmol)
 Final ligand concentration—[2.5 nM]
 Non-specific determinant: 5-Carboxamidotryptamine (5-CT)—[0.1 µM]
  Reference compound: 5-Carboxamidotryptamine
  Positive control: 5-Carboxamidotryptamine Incubation Conditions:

Reactions are carried out in 50 mM TRIS-HCl (pH 7.4) containing 10 mM $MgCl_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin-$5HT_7$ binding site.

LITERATURE REFERENCE

Y. Shen, E. Monsma, M. Metcalf, P. Jose, M Hamblin, D. Sibley, Molecular Cloning and Expression of a 5-hydroxytryptamine7 Serotonin Receptor Subtype. J. Biol. Chem. 268: 18200-18204.

The following description illustrates the method of preparation of variously substituted compounds of general formula (I), according to the methods described herein. These are provided by the way of illustration only and therefore should not be construed to limit the scope of the invention.

Commercial reagents were utilized without further purification. Room temperature refers to 25-30° C. Melting points are uncorrected. IR spectra were taken using KBr and in solid state. Unless otherwise stated, all mass spectra were carried out using ESI conditions. 1H NMR spectra were recorded at 300 MHz on a Bruker instrument. Deuterated chloroform (99.8% D) was used as solvent. TMS was used as internal reference standard. Chemical shift values are expressed in are reported in parts per million (δ)-values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. NMR, mass were corrected for background peaks. Specific rotations were measured at room temperature using the sodium D (589 nm). Chromatography refers to column chromatography performed using 60-120 mesh silica gel and executed under nitrogen pressure (flash chromatography) conditions.

Description 1: N,N-Dimethyl-1-(2'-bromobenzyl) tryptamine (D1)

A suspension of sodium hydride (9.0 mmoles, 0.36 g (60% suspension in mineral oil), washed with THF before use), in THF was stirred and cooled at 0-5° C. To this cooled solution was added a solution of N,N-dimethyltryptamine (6.0 mmoles), in THF, slowly, over 15 min., maintaining the temperature below 10° C. After completion of addtition, the mixture was warmed to 25-30° C. and maintained for 60 min. The reaction mixture was then cooled to 0-5° C. and solution of 2'-bromobenzyl bromide in THF (6.0 mmoles, 1.5 g in 7 mL of THF) was then added to the above well stirred mixture, maintaining the reaction temperature below 10° C. (Exothermic reaction). The reaction mixture was maintained at 20-25° C. for further 2-4 hrs. After completion of reaction (TLC), the excess of THF was distilled off and the concentrate was diluted with ice-water and extracted with ethyl acetate. Combined ethyl acetate layer was washed with water, dried over sodium sulfate and evaporated under reduced pressure, below 50° C.

The crude residue was purified by silica gel column chromatography using 30% methanol in ethyl acetate as a mobile phase, to obtain the intermediate, N,N-Dimethyl-1-(2'-bromobenzyl)tryptamine, which was identified by IR, NMR and mass spectral analyses.

Description 2-26 (D2- D26):

Various indole intermediates were treated with substituted 2-bromobenzyl bromide according to the procedure described in the description 1. These compounds were identified by IR, NMR and mass spectral analyses. The following list includes list of such compounds.

List-1:

| Description | | Mass ion (M + H)$^+$ |
|---|---|---|
| D1 | 2-[1-(2-Bromobenzyl)indol3-yl]ethyl-N,N-dimethylamine | 357 |
| D2 | 2-[1-(2-Bromobenzyl)-5-bromoindol3-yl]ethyl-N,N-dimethylamine | 435 |
| D3 | 2-[1-(2-Bromobenzyl)-7-bromoindol3-yl]ethyl-N,N-dimethylamine | 435 |
| D4 | 2-[1-(2-Bromobenzyl)-5-chloroindol3-yl]ethyl-N,N-dimethylamine | 391 |
| D5 | 2-[1-(2-Bromobenzyl)-5-fluoroindol3-yl]ethyl-N,N-dimethylamine | 375 |
| D6 | 2-[1-(2-Bromobenzyl)-7-fluoroindol3-yl]ethyl-N,N-dimethylamine | 375 |

-continued

| | Description | Mass ion (M + H)+ |
|---|---|---|
| D7 | 2-[1-(2-Bromobenzyl)-5-methylindol3-yl]ethyl-N,N-dimethylamine | 371 |
| D8 | 2-[1-(2-Bromobenzyl)-5-methoxyindol3-yl]ethyl-N,N-dimethylamine | 387 |
| D9 | 2-[1-(2-Bromobenzyl)-7-methoxyindol3-yl]ethyl-N,N-dimethylamine | 387 |
| D10 | 2-[1-(2-Bromobenzyl)-5-bromoindol3-yl]ethyl-N,N-diethylamine | 463 |
| D11 | 2-[1-(2-Bromobenzyl)-5-bromoindol3-yl]ethyl-N-cyclopropyl-N-methylamine | 461 |
| D12 | 2-[1-(2-Bromobenzyl)-7-chloroindol3-yl]ethyl-N,N-dimethylamine | 391 |
| D13 | 2-[1-(2-Bromobenzyl)-6,7-dichloroindol3-yl]ethyl-N,N-dimethylamine | 425 |
| D14 | 2-[1-(2-Bromobenzyl)-4-chloro-7-methylindol3-yl]ethyl-N,N-dimethylamine | 405 |
| D15 | 2-[1-(2-Bromobenzyl)-6-chloro-7-methylindol3-yl]ethyl-N,N-dimethylamine | 405 |
| D16 | 2-[1-(2-Bromobenzyl)-7-trifluoromethylindol3-yl]ethyl-N,N-dimethylamine | 425 |
| D17 | 2-[1-(2-Bromobenzyl)-5,7-difluoroindol3-yl]ethyl-N,N-dimethylamine | 393 |
| D18 | 1-(2-Bromobenzyl)-3-(2-pyrrolidin-1-yl-ethyl)-1H-indole | 383 |
| D19 | 1-(2-Bromobenzyl)-5-bromo-3-(2-(pyrrolidin-1-yl)ethyl)-1H-indole | 461 |
| D20 | 1-(2-Bromobenzyl)-5-bromo-3-(2-(piperidin-1-yl)ethyl)-1H-indole | 475 |
| D21 | 1-(2-Bromobenzyl)-(2-(4-methylpiperazin-1-yl)ethyl)-1H-indole | 412 |
| D22 | 1-(2-Bromobenzyl)-5-bromo-3-(3-(pyrrolidin-1-yl)-1-hydroxypropyl)-1H-indole | 491 |
| D23 | 1-(2-Bromobenzyl)-5-bromo-3-(3-(piperidin-1-yl)-1-hydroxypropyl)-1H-indole | 505 |
| D24 | 2-[1-(2-Bromobenzyl)-7-ethylindol3-yl]ethyl-N,N-dimethylamine | 385 |
| D25 | 2-[1-(2-Bromobenzyl)indol3-yl]-1-hydroxyethyl-N,N-dimethylamine | 373 |
| D26 | 1-(2-Bromobenzyl)-5-bromo-3-(2-(4-methylpiperazin-1-yl)ethyl)-1H-indole | 490 |

EXAMPLE-1

11-(2-N,N-Dimethylaminoethyl)-6H-isoindolo[2,1-a]indole 1-(2'-bromobenzyl)-N,N-dimethyltryptamine (0.286 mmoles, 0.102 g) was taken in a 100 mL 3 necked round bottomed flask, along with N,N-dimethyl acetamide (40 mL), potassium acetate (0.286 mmoles, 0.281 g) and dichloro bis(tri-o-tolylphosphine)palladium (0.0143 mmoles, 0.01123 g). The reaction mixture was maintained under nitrogen atmosphere and was heated to 140-160° C. with stirring for 3-4 hrs. After the completion of reaction (TLC), excess of dimethyl acetamide was distilled off under reduced pressure.

The residue obtained was purified by silica gel column chromatography using 20% methanol in ethyl acetate as an eluent, to afford the title compound, which was identified by IR, NMR and mass spectral analyses. The final desired compound of general formula (I) can be further purified by preparation of their acid addition salts. Melting range (° C.): 94-96; IR spectra (cm$^{-1}$): 2942, 2762, 1458, 1443; Mass (m/z): 277 (M+H)$^+$; $^1$H-NMR (δ ppm): 2.4 (6H, s), 2.60-2.68 (2H, m), 3.17-3.26 (2H, m), 5.0 (2H, s), 7.10-7.77 (8H, m).

EXAMPLE-2

2-Chloro-11-(2-N,N-dimethylaminoethyl)-6H-isoindolo[2,1-a]indole

Using essentially the general procedure described in example 1 and some non-critical variations, the above derivative was prepared. Melting range (° C.): 76-78; IR spectra (cm$^{-1}$): 2938, 2778, 1469, 1445; Mass (m/z): 311 (M+H)$^+$; $^1$H-NMR (δ ppm): 2.37 (6H, s), 2.59-2.63 (2H, m), 3.12-3.18 (2H, m), 5.01 (2H, s), 7.07-7.75 (8H, m).

EXAMPLE-3

2-Chloro-11-(2-N,N-dimethylaminoethyl)-6H-isoindolo[2,1-a]indole hydrochloride salt Example no. 2 (236 mg) was dissolved in 30 mL ether. To this clear solution a mixture of isopropylalcohol-hydrochloric acid (10 mL) was added. Immediately a white precipitate separates out, which was filtered, washed with ether and dried. Melting range (° C.): >250 (dec).

EXAMPLE-4

2-Chloro-11-(2-N,N-dimethylaminoethyl)-6H-isoindolo[2,1-a]indole maleic acid salt Example no. 2 (228 mg) was dissolved in 30 mL ether. To this clear solution a solution of maleic acid (90 mg, dissolved in 30 mL ether+5 mL methanol) was added. Immediately a white precipitate separates out, which was filtered, washed with ether and dried. Melting range (° C.): 202-204 (dec).

EXAMPLE-5

2-Chloro-11-(2-N,N-dimethylaminoethyl)-6H-isoindolo[2,1-a]indole D,L-malic acid salt Example no. 2 (190 mg) was dissolved in 30 mL ether. To this clear solution a solution of D,L-malic acid (86 mg, dissolved in 30 mL ether+5 mL methanol) was added. Immediately a white precipitate separates out, which was filtered, washed with ether and dried. Melting range (° C.): 173-176 (dec).

EXAMPLE-6

2-Chloro-11-(2-N,N-dimethylaminoethyl)-6H-isoindolo[2,1-a]indole oxalate salt

Example no. 2 (198 mg) was dissolved in 30 mL ether. To this clear solution a solution of oxalic acid (86 mg, dissolved in 30 mL ether+5 mL methanol) was added. Immediately a white precipitate separates out, which was filtered, washed with ether and dried. Melting range (° C.): 222-224 (dec).

EXAMPLE-7

2-Chloro-11-(2-N,N-dimethylaminoethyl)-6H-isoindolo[2,1-a]indole citrate salt

Example no. 2 (213 mg) was dissolved in 30 mL ether. To this clear solution a solution of citric acid (133 mg, dissolved in 30 mL ether+5 mL methanol) was added. Immediately a white precipitate separates out, which was filtered, washed with ether and dried. Melting range (° C.): 150-152 (dec).

EXAMPLE-8

2-Fluoro-11-(2-N,N-dimethylaminoethyl)-6H-isoindolo[2,1-a]indole

Using essentially the general procedure described in example 1 and some non-critical variations, the above derivative was prepared. Melting range (° C.): 96-100; IR spectra (cm$^{-1}$): 2941, 2784, 1458, 798; Mass (m/z): 295 (M+H)$^+$; $^1$H-NMR (δ ppm): 2.38 (6H, s), 2.560-2.65 (2H, m), 3.11-3.19 (2H, m), 5.02 (2H, s), 6.91-7.77 (8H, m).

EXAMPLE-9

11-(2-N,N-Dimethylaminoethyl)-2-methyl-6H-isoindolo[2,1-a]indole

Using essentially the general procedure described in example 1 and some non-critical variations, the above derivative was prepared. Melting range (° C.): 102-106; IR spectra (cm−1): 2934, 2761, 1439, 765; Mass (m/z): 291 (M+H)$^+$; $^1$H-NMR (δ ppm): 2.38 (6H, s), 2.46 (3H, s), 2.56-2.65 (2H, m), 3.12-3.20(2H, m), 4.99 (2H, s), 6.98-7.73 (7H, m).

EXAMPLE-10

11-(2-N,N-Dimethylaminoethyl)-2-methoxy-6H-isoindolo[2,1-a]indole

Using essentially the general procedure described in example 1 and some non-critical variations, the above derivative was prepared. Melting range (° C.): 140-143; IR spectra (cm−1): 2903, 2781, 1621, 1459, 769; Mass (m/z): 307 (M+H)$^+$; $^1$H-NMR (δ ppm): 2.40 (6H, s), 2.57-2.66 (2H, m), 3.13-3.21 (2H, m), 3.88 (3H, s), 5.00 (2H, s), 6.82-7.73 (7H, m).

EXAMPLE-11

2-Bromo-11-(2-N,N-diethylaminoethyl)-6H-isoindolo[2,1-a]indole

Using essentially the general procedure described in example 1 and some non-critical variations, the above derivative was prepared. IR spectra (cm−1): 2964, 1613, 1444, 1261, 795; Mass (m/z): 383 (M+H)$^+$.

EXAMPLE-12

2-Bromo-11-(2-N-methyl-N-cyclopropylaminoethyl)-6H-iso indolo[2,1-a]indole

Using essentially the general procedure described in example 1 and some non-critical variations, the above derivative was prepared. IR spectra (cm−1): 2926, 1469, 1358, 1169, 793; Mass (m/z): 381 (M+H)$^+$; $^1$H-NMR (δ ppm): 0.44-0.61 (4H,m), 1.82-1.87 (1H, m), 2.48 (3H, s), 2.72-2.80 (2H, m), 2.95-3.07 (2H, m), 5.25 (2H, s), 7.06-7.32 (7H, m).

EXAMPLE-13

4Chloro-11-(2-N,N-dimethylaminoethyl)-6H-isoindolo[2,1-a]indole

Using essentially the general procedure described in example 1 and some non-critical variations, the above derivative was prepared. IR spectra (cm$^{-1}$): 2938, 2778, 1469, 1445; Mass (m/z): 311 (M+H)$^+$.

EXAMPLE-14

3,4-Dichloro-11-(2-N,N-dimethylaminoethyl)-6H-isoindolo[2,1-a]indole

Using essentially the general procedure described in example 1 and some non-critical variations, the above derivative was prepared. Mass (m/z): 345 (M+H)$^+$.

EXAMPLE-15

1-Chloro-11-(2-N,N-dimethylaminoethyl)-4-methyl-6H-isoindolo[2,1-a]indole

Using essentially the general procedure described in example 1 and some non-critical variations, the above derivative was prepared. Mass (m/z): 325 (M+H)$^+$.

EXAMPLE-16

3-Chloro-11-(2-N,N-dimethylaminoethyl)-4-methyl-6H-isoindolo[2,1-a]indole

Using essentially the general procedure described in example 1 and some non-critical variations, the above derivative was prepared. Mass (m/z): 325 (M+H)$^+$.

EXAMPLE-17

11-(2-N,N-Dimethylaminoethyl)-4-trifluoromethyl-6H-isoindolo[2,1-a]indole

Using essentially the general procedure described in example 1 and some non-critical variations, the above derivative was prepared. Mass (m/z): 345 (M+H)$^+$.

EXAMPLE-18

2,4-Difluoro-11-(2-N,N-dimethylaminoethyl)-6H-isoindolo[2,1-a]indole

Using essentially the general procedure described in example 1 and some non-critical variations, the above derivative was prepared. Melting range (° C.): 84-86; IR' spectra (cm$^{-1}$): 2941, 2784, 1458, 798; Mass (m/z): 313 (M+H)$^+$; $^1$H-NMR(δ ppm): 2.38 (6H, m), 2.55-2.63 (2H, m), 3.09-3.17 (2H, m), 5.22 (2H, s), 6.63-7.78 (6H, m).

EXAMPLE-19

11-(2-Pyrrolidin-1-ylethyl)-6H-isoindolo[2,1-a]indole

Using essentially the general procedure described in example 1 and some non-critical variations, the above derivative was prepared. Melting range (° C.): 86-90; IR spectra (cm$^{-1}$): 2832, 2807, 1361, 1334; Mass (m/z): 303 (M+H)$^+$; $^1$H-NMR (δ ppm): 1.79-1.85 (4H, m), 2.55-2.68 (6H, m), 2.75-2.82 (2H, m), 5.28 (2H, s), 7.10-7.34 (8H, m).

EXAMPLE-20

2-Bromo-11-(2-pyrrolidin-1-ylethyl)-6H-isoindolo[2,1-a]indole

Using essentially the general procedure described in example 1 and some non-critical variations, the above derivative was prepared. Mass (m/z): 381 (M+H)$^+$.

EXAMPLE-21

11-(2-(Piperidin-1-yl)ethyl)-6H-isoindolo[2,1-a]indole

Using essentially the general procedure described in example 1 and some non-critical variations, the above derivative was prepared.
Melting range (° C.): 102-104; IR spectra (cm$^{-1}$): 2929, 2840, 1455, 1162; Mass (m/z): 317 (M+H)$^+$; $^1$H-NMR (δ ppm): 1.44-1.52 (2H, m), 1.60-1.66 (4H, m), 2.38-2.43 (2H, m), 2.64-2.76 (6H, m), 5.28 (2H, s), 7.08-7.73 (8H, m).

EXAMPLE-22

11-(2-(4-Methylpiperazin-1-yl)ethyl)-6H-isoindolo[2,1-a]indole

Using essentially the general procedure described in example 1 and some non-critical variations, the above derivative was prepared. IR spectra (cm$^{-1}$): 2937, 2803, 1634, 1455; Mass (m/z): 332 (M+H)$^+$.

EXAMPLE-23

11-(3-(Pyrrolidin-1-yl)-1-hydroxyprop-1-yl)-6H-isoindolo[2,1-a]indole

Using essentially the general procedure described in example 1 and some non-critical variations, the above derivative was prepared. Mass (m/z): 333 (M+H)$^+$.

EXAMPLE-24

2-Bromo-11-(3-(piperidin-1-yl)-1-hydroxyprop-1-yl)-6H-isoindolo[2,1-a]indole

Using essentially the general procedure described in example 1 and some non-critical variations, the above derivative was prepared. Mass (m/z): 425 (M+H)$^+$.

EXAMPLE-25

11-(2-N,N-Dimethylaminoethyl)-4-ethyl-6H-isoindolo[2,1-a]indole

Using essentially the general procedure described in example 1 and some non-critical variations, the above derivative was prepared. Mass (m/z): 305 (M+H)$^+$.

EXAMPLE-26

11-(2-N,N-Dimethylamino-1-hydroxyethyl)-6H-isoindolo[2,1-a]indole

Using essentially the general procedure described in example 1 and some non-critical variations, the above derivative was prepared. Mass (m/z): 293 (M+H)$^+$.

EXAMPLE-27

11-(2-N,N-Dimethylaminoethyl)-4-methoxy-6H-isoindolo[2,1-a]indole

Using essentially the general procedure described in example 1 and some non-critical variations, the above derivative was prepared. Mass (m/z): 307 (M+H)$^+$.

EXAMPLE-28

2-Bromo-11-(2-N,N-dimethylaminoethyl)-6H-isoindolo[2,1-a]indole

Using essentially the general procedure described in example 1 and some non-critical variations, the above derivative was prepared. Mass (m/z): 355 (M+H)$^+$.

EXAMPLE-29

4-Bromo-11-(2-N,N-dimethylaminoethyl)-6H-isoindolo[2,1-a]indole

Using essentially the general procedure described in example 1 and some non-critical variations, the above derivative was prepared. Mass (m/z): 355 (M+H)$^+$.

EXAMPLE-30

4-Fluoro-11-(2-N,N-dimethylaminoethyl)-6H-isoindolo[2,1-a]indole

Using essentially the general procedure described in example 1 and some non-critical variations, the above derivative was prepared. Mass (m/z): 295 (M+H)$^+$.

EXAMPLE-31

2-Bromo-11-(2-(4-methylpiperazin-1-yl)ethyl)-6H-isoindolo[2,1-a]indole

Using essentially the general procedure described in example 1 and some non-critical variations, the above derivative was prepared. Mass (m/z) 410 (M+H)$^+$.

The invention claimed is:
1. A compound of the general formula (I),

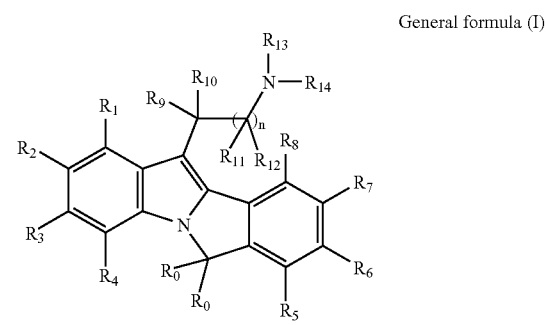

General formula (I)

wherein
$R_0$ is hydrogen or a ($C_1$-$C_2$)alkyl;
$R_1$, $R_2$, $R_3$, $R_4$, $R_5$, $R_6$, $R_7$, $R_8$, $R_9$, $R_{10}$, $R_{11}$ and $R_{12}$ are the same or different and are each independently selected from the group consisting of hydrogen, a halogen, a perhaloalkyl group, an amino group, a substituted or unsubstituted linear or branched chain ($C_1$-$C_{12}$)alkyl, ($C_3$-$C_7$)cycloalkyl, ($C_1$-$C_{12}$)alkoxy, cyclo($C_3$-$C_7$)alkoxy, aryl, aryloxy, aralkyl, aralkoxy, heterocyclyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, hydroxyalkyl, aminoalkyl, monoalkylaminoalkyl, dialkylaminoalkyl, alkoxyalkyl, alkylthio, aminocarbonylamino, dialkylaminocarbonylamino, carboxylic acid and derivatives thereof;

$R_{13}$ and $R_{14}$ are the same or different and are each independently selected from the group consisting of hydrogen, a substituted or unsubstituted linear or branched chain ($C_1$-$C_4$)alkyl, ($C_3$-$C_7$)cycloalkyl, ($C_3$-$C_7$)cycloalkenyl, bicycloalkyl, bicycloalkenyl, aryl, and aralkyl, or $R_{13}$ and $R_{14}$ taken together with the nitrogen atom to which they are attached, form a substituted or unsubstituted 3, 4, 5, 6 or 7-membered heterocyclic ring, wherein said ring contains from 0 to 3 double bonds and from 0 to 2 hetero atoms; and n is an integer ranging from 1 to 6, wherein if n is an integer ranging from 3 to 6, the carbon chain is linear or branched, or a tautomeric form, stereoisomer, or pharmaceutically acceptable salt thereof.

2. The compound according to claim 1, which is selected from the group consisting of:

11-(2-N,N-Dimethylaminoethyl)-6H-isoindolo[2,1-a]indole;
2-Chloro-11-(2-N,N-dimethylaminoethyl)-6H-isoindolo[2,1-a]indole;
2-Chloro-11-(2-N,N-dimethylaminoethyl)-6H-isoindolo[2,1-a]indole hydrochloride salt;
2-Chloro-11-(2-N,N-dimethylaminoethyl)-6H-isoindolo[2,1-a]indole maleic acid salt;
2-Chloro-11-(2-N,N-dimethylaminoethyl)-6H-isoindolo[2,1-a]indole D,L-malic acid salt;
2-Chloro-11-(2-N,N-dimethylamino-ethyl)-6H-isoindolo[2,1-a]indole oxalate salt;
2-Chloro-11-(2-N,N-dimethyl-aminoethyl)-6H-isoindolo[2,1-a]indole citrate salt;
2-Fluoro-11-(2-N,N-dimethylaminoethyl)-6H-isoindolo[2,1-a]indole;
2-Chloro-11-(2-N,N-diethylaminoethyl)-6H-isoindolo[2,1-a]indole citrate salt;
2-Fluoro-11-(2-N,N-diethylaminoethyl)-6H-isoindolo[2,1-a]indole;
2-Chloro-11-(2-N-cyclopropyl-N-methylaminoethyl)-6H-isoindolo[2,1-a]indole citrate salt;
2-Fluoro-11-(2-N-cyclopropyl-N-methylaminoethyl)-6H-isoindolo[2,1-a]indole;
11-(2-N,N-Dimethylaminoethyl)-2-methyl-6H-isoindolo[2,1-a]indole;
11-(2-N,N-Dimethylaminoethyl)-2-methoxy-6H-isoindolo[2,1-a]indole;
2-Bromo-11-(2-N,N-diethylaminoethyl)-6H-isoindolo[2,1-a]indole;
2-Bromo-11-(2-N-methyl-N-cyclopropylaminoethyl)-6H-isoindolo[2,1-a]indole;
4-Chloro-11-(2-N,N-dimethylaminoethyl)-6H-isoindolo[2,1-a]indole;
3,4-Dichloro-11-(2-N,N-dimethylaminoethyl)-6H-isoindolo[2,1-a]indole;
1-Chloro-11-(2-N,N-dimethylaminoethyl)-4methyl-6H-isoindolo[2,1-a]indole;
3-Chloro-11-(2-N,N-dimethylaminoethyl)-4methyl-6H-isoindolo[2,1-a]indole;
3-Chloro-11-[(2-N-methylamino)ethyl]-4-methyl-6H-isoindolo[2,1-a]indole;
3-Chloro-11-[(2-N-methyl-N-acetylamino)ethyl]-4methyl-6H-isoindolo[2,1-a]indole;
3-Chloro-11-[(2-N-methylamino)ethyl]-2-methoxy-6H-isoindolo[2,1-a]indole;
3-Chloro-11-[(2-N-methylamino)ethyl]-2-sulfoamido-6H-isoindolo[2,1-a]indole;
3-Iodo-11-[(2-N-methylamino)ethyl]-2-methoxy-6H-isoindolo[2,1-a]indole;
11-(2-N,N-Dimethylaminoethyl)-4-trifluoromethyl-6H-isoindolo[2,1-a]indole;
2,4-Difluoro-11-(2-N,N-dimethylaminoethyl)-6H-isoindolo[2,1-a]indole;
11-(2-Pyrrolidin-1-ylethyl)-6H-isoindolo[2,1-a]indole;
2-Bromo-11-(2-pyrrolidin-1-ylethyl)-6H-isoindolo[2,1-a]indole;
11-(2-(Piperidin-1-yl)ethyl)-6H-isoindolo[2,1-a]indole;
11-(2-(4-Methylpiperazin-1-yl)ethyl)-6H-isoindolo[2,1-a]indole;
11-(3-(Pyrrolidin-1-yl)-1-hydroxyprop-1-yl)-6H-isoindolo[2,1-a]indole;
2-Bromo-11-(3-(piperidin-1-yl)-1-hydroxyprop-1-yl)-6H-isoindolo[2,1-a]indole;
11-(2-N,N-Dimethylaminoethyl)-4-ethyl-6H-isoindolo[2,1-a]indole;
11-(2-N,N-Dimethylamino-1-hydroxyethyl)-6H-isoindolo[2,1-a]indole;
11-(2-N,N-Dimethylaminoethyl)-4-methoxy-6H-isoindolo[2,1-a]indole;
2-Bromo-11-(2-N,N-dimethylaminoethyl)-6H-isoindolo[2,1-a]indole;
4-Bromo-11-(2-N,N-dimethylaminoethyl)-6H-isoindolo[2,1-a]indole;
4-Fluoro-11-(2-N,N-dimethylaminoethyl)-6H-isoindolo[2,1-a]indole;
2-Bromo-11-(2-(4methylpiperazin-1-yl)ethyl)-6H-isoindolo[2,1-a]indole; and stereoisomers, N-oxides, and pharmaceutically acceptable salts thereof.

3. A pharmaceutical composition comprising either of a pharmaceutically acceptable carrier, diluent, excipient or solvates along with a therapeutically effective amount of a compound according to claim 1.

4. The pharmaceutical composition according to claim 3, which is in the form of a tablet, capsule, powder, lozenges, suppositories, syrup, solution, suspension or an injectable, wherein said form is administered in a single dose or multiple dose units.

5. A method of modulating 5-HT and melatonin activity in a patient, comprising administering to said patient a therapeutically effective amount of a compound according to claim 1.

6. A method of selectively modulating the 5-HT receptors of a patient, comprising administering to said patient a therapeutically effective amount of a compound according to claim 1.

7. A method of modulating 5-HT receptor function in a patient, comprising administering to said patient a therapeutically effective amount of a compound according to claim 1, wherein the compound is isotopically labeled.

8. The pharmaceutical composition according to claim 3, further comprising a therapeutically effective amount of a 5-HT re-uptake inhibitor, melatonin, a melatoninergic modulator or a pharmaceutically acceptable salt thereof.

9. A method for the treatment of anxiety, depression, convulsive disorders, obsessive-compulsive disorders, migraine headache, cognitive memory disorders, Attention Deficient Disorder/Hyperactivity Syndrome, personality disorders, psychosis, paraphrenia, psychotic depression, mania, schizophrenia, schizophreniform disorders, withdrawal from drug abuse, panic attacks, reproduction, glaucoma, sleep disorders or disorders associated with spinal trauma or head injury in a patient, which comprises administering to said patient in need thereof a therapeutically effective amount of a compound according to claim 1.

10. A method for the treatment of mild cognitive impairment, Alzheimer's disease, Parkinsonism or Huntington's chorea in a patient, which comprises administering to said patient in need thereof a therapeutically effective amount of a compound according to claim 1.

11. A method for the treatment of irritable bowel syndrome or chemotherapy induced emesis in a patient, comprising administering to said patient a therapeutically effective amount of a compound according to claim 1.

12. A method of reducing in a patient morbidity and mortality associated with excess weight, comprising administering to the patient a therapeutically effective amount of a compound according to claim 1.

\* \* \* \* \*